US012751734B2

(12) United States Patent
Inoue et al.

(10) Patent No.: US 12,751,734 B2
(45) Date of Patent: Oct. 6, 2026

(54) REPLACEABLE SURGICAL SCISSOR BLADES FOR SURGICAL INSTRUMENTS

(71) Applicant: Cilag GmbH International, Zug (CH)

(72) Inventors: Shinnosuke Inoue, Daily City, CA (US); Samuel Gerard Selle, Milpitas, CA (US)

(73) Assignee: CILAG GMBH INTERNATIONAL, Zug (CH)

( * ) Notice: Subject to any disclaimer, the term of this patent is extended or adjusted under 35 U.S.C. 154(b) by 148 days.

(21) Appl. No.: 18/787,475

(22) Filed: Jul. 29, 2024

(65) Prior Publication Data

US 2026/0026868 A1 Jan. 29, 2026

(51) Int. Cl.
*A61B 17/3201* (2006.01)
*A61B 17/00* (2006.01)
(Continued)

(52) U.S. Cl.
CPC ...... *A61B 17/3201* (2013.01); *A61B 18/1445* (2013.01); *A61B 34/71* (2016.02);
(Continued)

(58) Field of Classification Search
CPC ............ A61B 18/1445; A61B 17/3201; A61B 2017/00367; A61B 2017/2932;
(Continued)

(56) References Cited

U.S. PATENT DOCUMENTS 6,206,903 B1 * 3/2001 Ramans ................. A61B 17/29 606/205
10,751,140 B2 * 8/2020 Wallace ................. A61B 34/71
(Continued)

FOREIGN PATENT DOCUMENTS

WO 2016025132 A1 2/2016
WO 2019236450 A1 12/2019
(Continued)

OTHER PUBLICATIONS

International Search Report and Written Opinion, Received for PCT Application No. PCT/IB2025/057610, Mailed on Nov. 7, 2025, 16 Pages.

*Primary Examiner* — Sarah A Long
(74) *Attorney, Agent, or Firm* — Joshua D. Young

(57) ABSTRACT

A surgical tool includes a drive housing, a shaft extending from the drive housing, wrist arranged at an end of the shaft and including a distal clevis, an axle mounted to the distal clevis, and first and second actuation pulleys rotatably mounted to the axle and rotatable about a pivot axis extending through the axle, each actuation pulley providing an actuation boss eccentric to the pivot axis, and an end effector operatively coupled to the wrist and including first and second blades pivotably coupled to the actuation bosses of the actuation pulleys. The blades are movable between open and closed positions by rotating the actuation pulleys such that the actuation boss of each actuation pulley remains proximal to a centerline of the axle, and movable to an over-centered position by rotating the actuation pulleys such that the actuation boss of each actuation pulley is located distal to the centerline.

20 Claims, 11 Drawing Sheets

(51) Int. Cl.

| | |
|---|---|
| ***A61B 18/14*** | (2006.01) |
| ***A61B 34/00*** | (2016.01) |
| *A61B 17/29* | (2006.01) |

(52) U.S. Cl.
CPC ............... *A61B 2017/00367* (2013.01); *A61B 2017/2932* (2013.01); *A61B 2017/2947* (2013.01); *A61B 2018/146* (2013.01)

(58) Field of Classification Search
CPC .... A61B 2017/2947; A61B 2017/2926; A61B 2017/00477; A61B 34/71; A61B 34/37; A61B 2018/146; A61B 2034/305
See application file for complete search history.

(56) References Cited

U.S. PATENT DOCUMENTS

| | | | | |
|---|---|---|---|---|
| 12,453,572 | B2 * | 10/2025 | Inoue | A61B 17/3201 |
| 2010/0191251 | A1 * | 7/2010 | Scott | A61B 18/14 606/130 |
| 2010/0198231 | A1 | 8/2010 | Scott | |
| 2019/0105099 | A1 | 4/2019 | Murrell et al. | |

FOREIGN PATENT DOCUMENTS

| | | | |
|---|---|---|---|
| WO | 2021163468 | A1 | 8/2021 |
| WO | 2023079432 | A1 | 5/2023 |

* cited by examiner

REPLACEABLE SURGICAL SCISSOR BLADES FOR SURGICAL INSTRUMENTS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable “wrist” joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some end effectors include high-wear components that can mechanically or physically degrade over time and thereby limit the useful life of the end effector. One example of high-wear components is the blades of surgical scissors, which can dull over time, and thereby adversely affect the efficiency of the end effector. What is needed is a method and system of more easily replacing the blades of an end effector, which can provide a user (e.g., a surgeon, a nurse, etc.) with a new set of blades for every new use of the surgical tool.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 12A, 12B and 2C depicts a sequence of removal of a component from an end effector according to one or more embodiments.

DETAILED DESCRIPTION

The present disclosure is related to robotic surgical systems and, more particularly, to methods and systems of replacing blades of end effector surgical scissors.

The embodiments disclosed herein describe a surgical tool with a drive housing and an elongate shaft extending distally from the drive housing. A wrist is arranged at a distal end of the shaft and includes a distal clevis, an axle mounted to the distal clevis, and first and second actuation pulleys rotatably mounted to the axle and rotatable about a pivot axis extending through the axle. Each actuation pulley provides an actuation boss eccentric to the pivot axis. An end effector is operatively coupled to the wrist and includes a first blade pivotably coupled to the actuation boss of the first actuation pulley, and a second blade rotatably coupled to the first blade at a center pin and pivotably coupled to the actuation boss of the second actuation pulley. The first and second blades are movable between open and closed positions by rotating the first and second actuation pulleys such that the actuation boss of each actuation pulley remains proximal to a centerline of the axle. The first and second blades are also movable to an over-centered position by rotating the first and second actuation pulleys such that the actuation boss of each actuation pulley is located distal to the centerline. Moving the first and second blades to the over-centered position exposes the actuation boss of each actuation pulley, thereby allowing the first and second blades to be removed and replaced.

Figure 1:
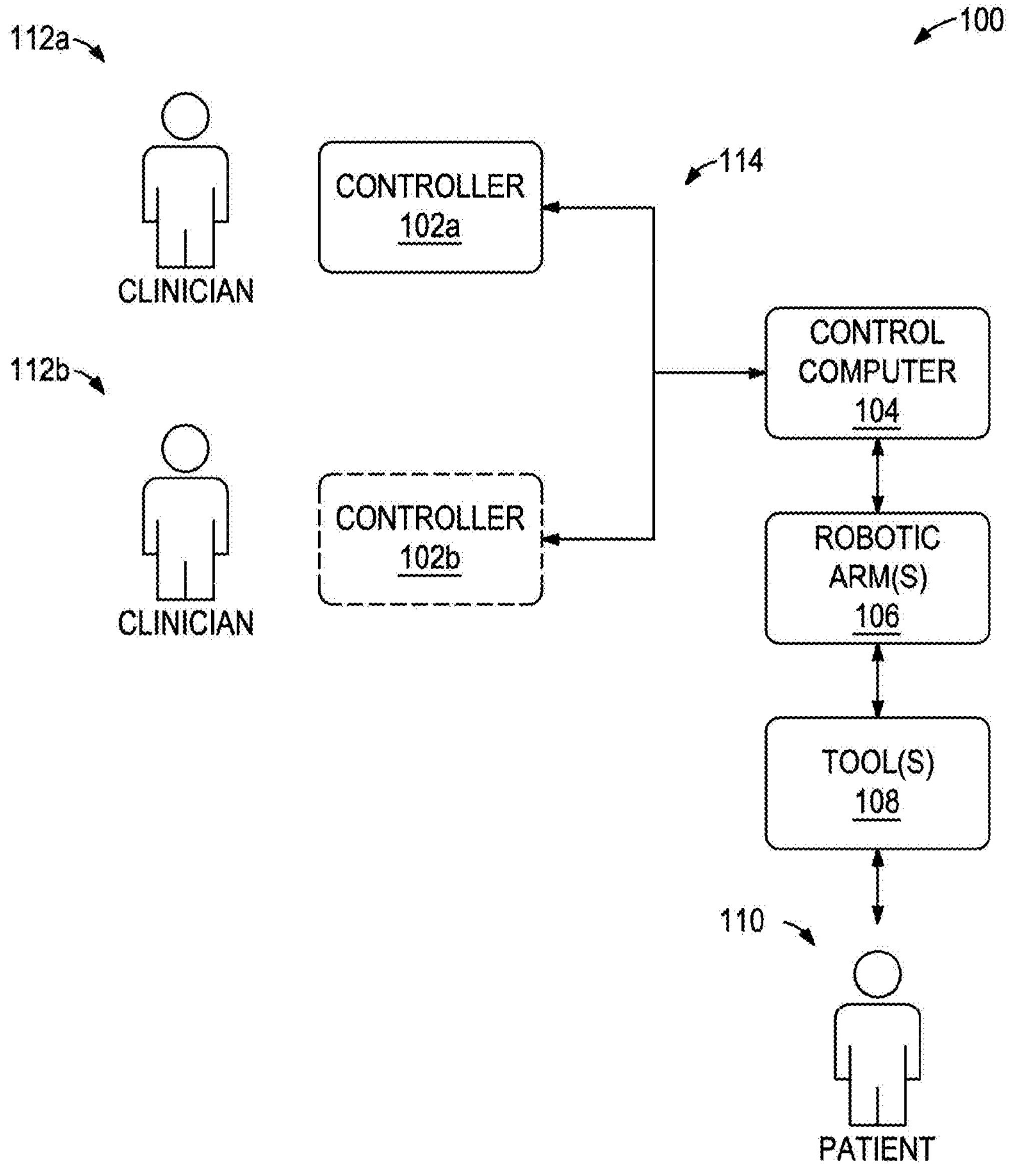
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as “tool drivers”). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms

106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws (or blades), applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
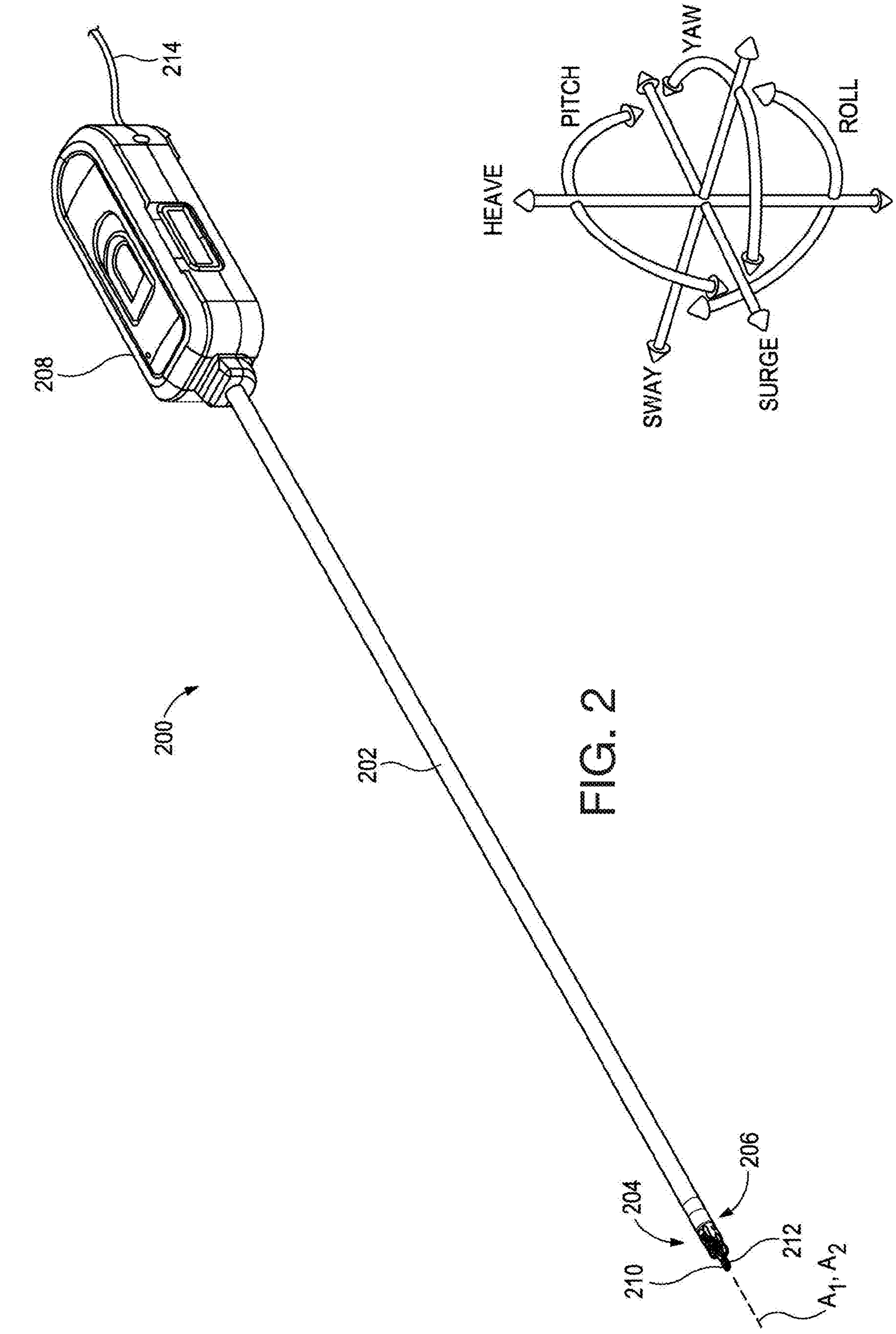
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises surgical scissors that includes opposing first (upper) and second (lower) blades 210, 212 configured to move (articulate) between open and closed positions. As will be appreciated, however, the blades 210, 212 may alternatively comprise opposing jaws that form part of other types of end effectors such as, but not limited to, a needle driver, a clip applier, a tissue grasper, a vessel sealer, a combination tissue grasper and vessel sealer, a babcock including a pair of opposed grasping jaws, bipolar jaws (e.g., bipolar Maryland grasper, forceps, a fenestrated grasper, etc.), etc. One or both of the blades 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto.

In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator that supplies energy, such as electrical energy (e.g., radio frequency energy), ultrasonic energy, microwave energy, heat energy, or any combination thereof, to the surgical tool 200 and, more particularly, to the end effector 204. Accordingly, the generator may comprise a radio frequency (RF) source, an ultrasonic source, a direct current source, and/or any other suitable type of electrical energy source that may be activated independently or simultaneously.

The surgical tool 200 may be configured for bipolar or monopolar operation. In bipolar operation, the power cable 214 will include a supply conductor and a return conductor. Current can be supplied from a generator (not shown) to the blades 210, 212 via the supply conductor, and current can flow back to the generator via a return conductor. In applications where the surgical tool 200 is configured for monopolar operation, the electrical energy may comprise radio frequency ("RF") energy exhibiting a frequency between about 100 kHz and 1 MHz. Low frequency RF energy causes ionic agitation or friction, in effect resistive heating, thereby increasing the temperature of target tissue. The electrical energy supplied to the end effector 204 is converted to heat and transferred to adjacent tissue to cut, cauterize, and/or coagulate the tissue (dependent upon the localized heating of the tissue), and thus may be particularly useful for sealing blood vessels or diffusing bleeding. Electrical energy (current) is then returned (dissipated) from the tissue through a return electrode, which typically comprises a grounding pad separately located on a patient's body.

Figure 4:
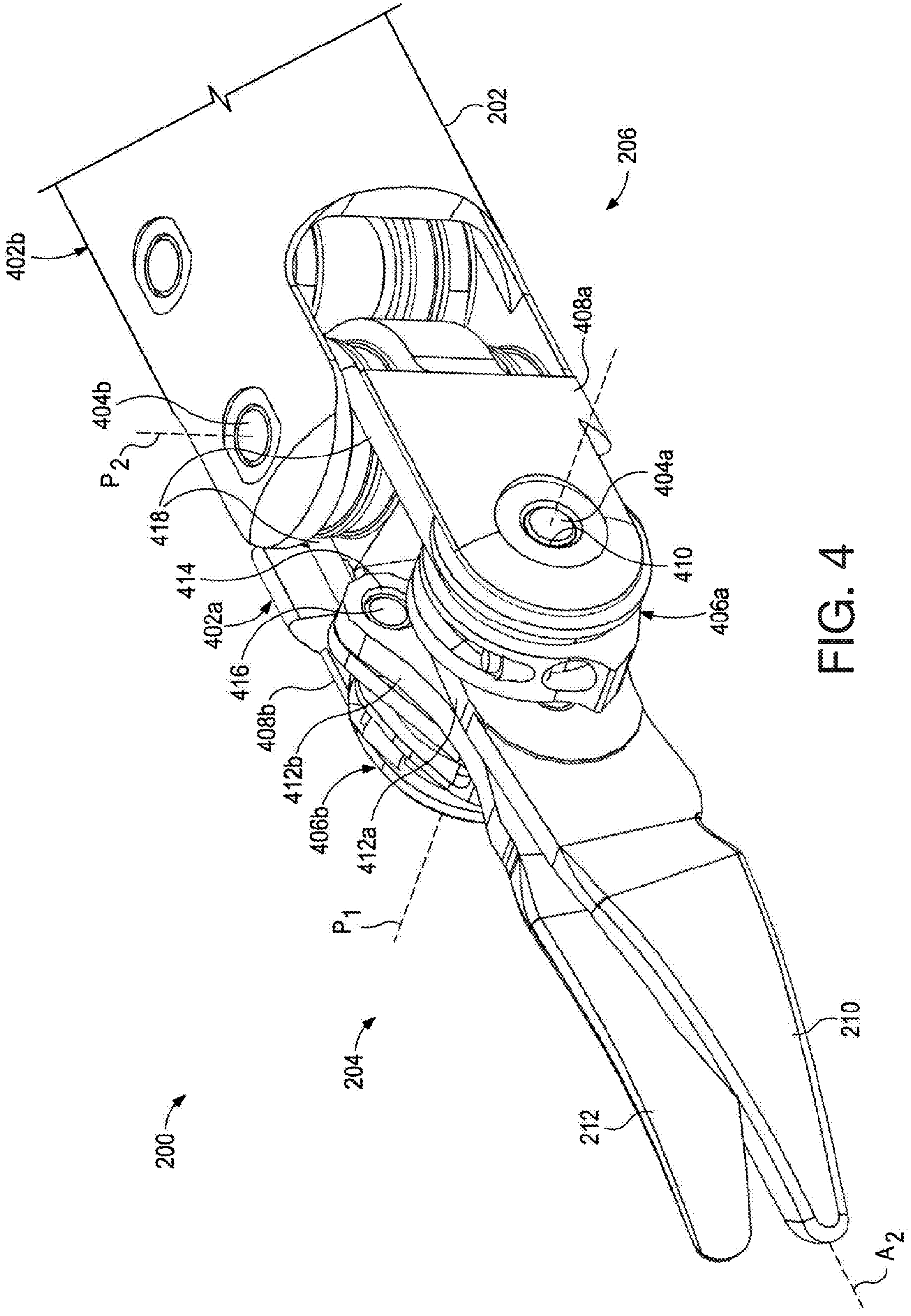
FIG. 4 is an enlarged isometric view of the distal end of the surgical tool of FIG. 2.

FIG. 4 is an enlarged isometric view of the distal end of the surgical tool 200, according to one or more embodiments. More specifically, FIG. 4 depicts enlarged views of the end effector 204 and the wrist 206, with the end effector 204 in the unarticulated position. The wrist 206 is operatively coupled to the end effector 204 and includes a distal clevis **402*a* and a proximal clevis 402*b*. The end effector 204 (i.e., the blades 210, 212) is rotatably mounted to the distal clevis 402*a* at a first axle 404*a*, and the distal clevis 402*a* is rotatably mounted to the proximal clevis 402*b* at a second axle 404*b*. The wrist 206 provides a first pivot axis $P_1$ that extends through the first axle 404*a* and a second pivot axis $P_2$ that extends through the second axle 404*b*. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "pitch" articulation of the end effector 204, and movement about the second pivot axis $P_2$ provides "yaw" articulation of the end effector 204**.

In the illustrated embodiment, the blades 210, 212 are actuatable between closed and open positions by movement at the first pivot axis $P_1$. More specifically, the end effector 204 includes first and second actuation pulleys **406*a* and 406*b* rotatably mounted to the distal clevis 402*a*. As illustrated, the distal clevis 402*a* includes a pair of distally-extending arms 408*a* and 408*b*, and the first axle 404*a* is mounted to corresponding apertures 410 (only one visible) defined in each arm 410*a,b*. The actuation pulleys 406*a,b* are mounted to the first axle 404*a* and rotatable about the first pivot axis $P_1$. Each blade 210, 212 provides or otherwise defines a proximally extending flange 412*a* and 412*b* (the first flange 412*a* is mostly occluded), respectively, and each flange 412*a,b* may be pivotably mounted to the corresponding (adjacent) actuation pulley 406*a,b*, respectively. Each flange 412*a,b* defines a flange aperture 414 (only one visible), and the corresponding actuation pulley 406*a,b* provides an actuation pin or "boss" 416 (only one visible) configured to be received within the flange aperture 414. Mounting the blades 210, 212 to the corresponding actuation pulley 406*a,b* allows the blades 210, 212 to rotate as the associated actuation pulley 406*a,b*** rotates.

While FIG. 4 shows the aperture 414 being provided by the flanges **414*a,b*, and the actuation bosses 416 being provided by the actuation pulleys 406*a,b*, in other embodiments the flanges 414*a,b* may instead provide the actuation boss and the actuation pulleys 406*a,b*** may alternatively provide an aperture that receives the actuation boss, without departing from the scope of the disclosure.

A plurality of drive cables 418 pass through the wrist 206 and terminate at the actuation pulleys **406*a,b*. The drive cables 418 form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 418** can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof.

The drive cables 418 extend proximally from the end effector 204 to the drive housing 208 (FIG. 2) where they are operatively coupled to various actuation mechanisms or devices housed (contained) therein to facilitate longitudinal movement (translation) of the drive cables 418. Selective actuation of all or some of the drive cables 418 causes the wrist 206 to articulate, causes the blades 210, 212 to open or close, or causes a combination of the foregoing. In at least one embodiment, the surgical tool 200 includes four drive cables 418, where a pair of drive cables 418 terminate at each actuation pulley 406*a,b*. The pairs of drive cables 418 may be configured to "antagonistically" operate to move the corresponding blade 210, 212. Accordingly, the drive cables 418 may be characterized or otherwise referred to as "antagonistic" cables that cooperatively (vet antagonistically) operate to cause relative or tandem movement of the actuation pulleys 406*a,b* and, therefore, relative or tandem movement of the blades 210, 212.

Figure 5A:
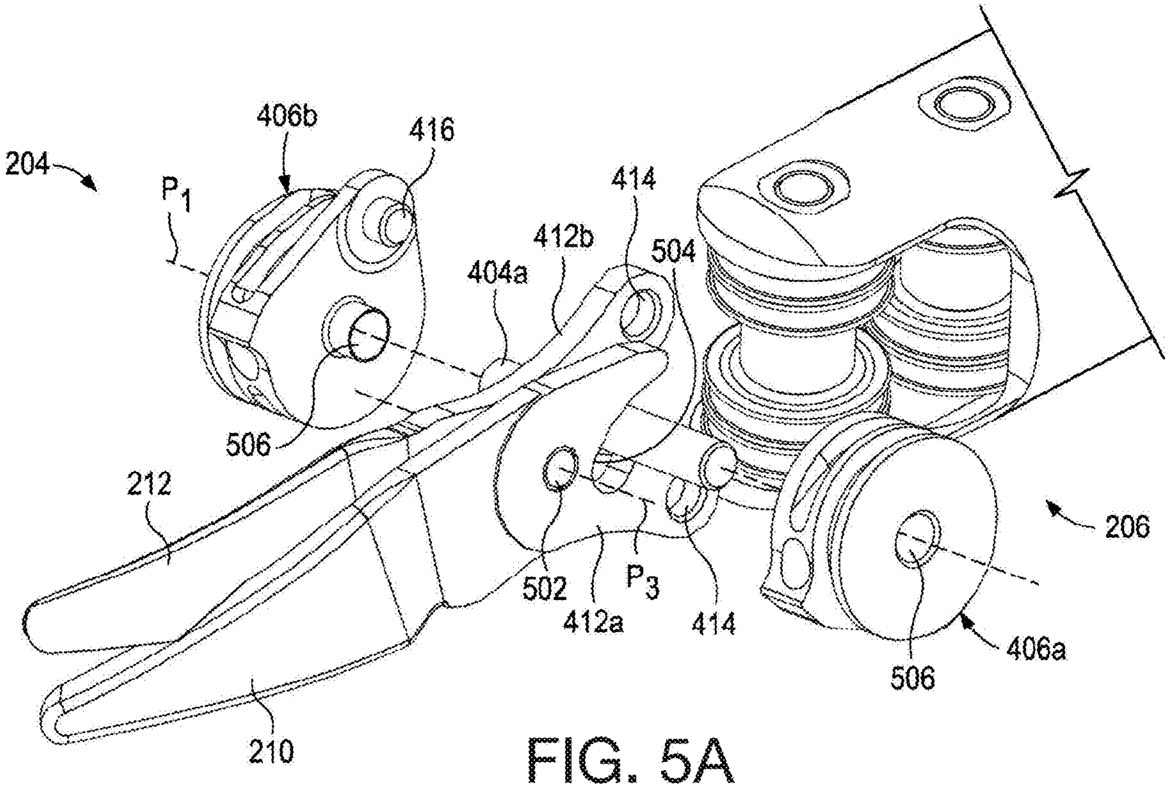
FIGS. 5A and 5B are right and left isometric views, respectively, of portions of the end effector and the wrist, according to one or more embodiments.
Figure 5B:
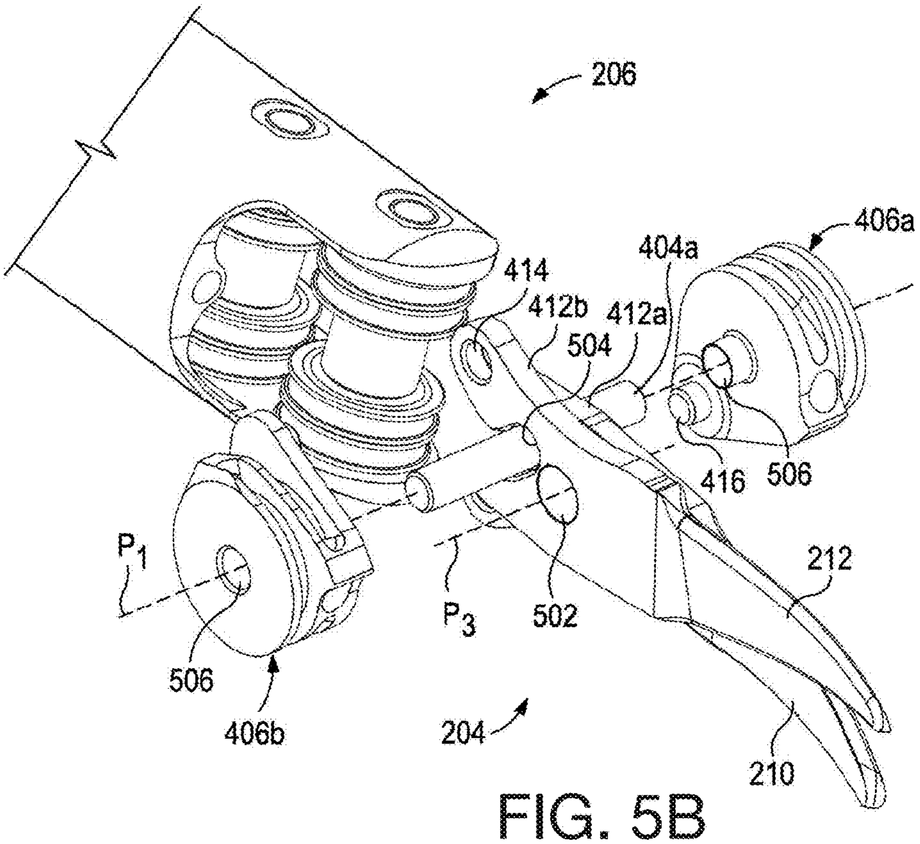

FIGS. 5A and 5B are right and left isometric views, respectively, of portions of the end effector 204 and the wrist 206, according to one or more embodiments. The distal clevis 402*a* (FIG. 4) and the drive cables 418 (FIG. 4) are omitted in FIGS. 5A-5B to enable viewing of various internal structures of the end effector 204.

As illustrated, the blades 210, 212 may be pinned and otherwise rotatably coupled to each other using a center pin 502, through which a third pivot axis $P_3$ extends. The third pivot axis $P_3$ extends generally parallel to the first pivot axis $P_1$, but is located distal to the first pivot axis $P_1$. The blades 210, 212 may be configured to rotate about the third pivot axis $P_3$ during opening and closing of the blades 210, 212, as described in more detail below.

As mentioned above, each blade 210, 212 provides a proximally extending flange 412*a,b*, respectively. Each blade 210, 212 may also provide and otherwise define an open-ended axle slot 504 configured to receive the first axle 404*a*. In some embodiments, the axle slot 504 may be at least partially defined in the flange 412*a,b* of each blade 210, 212. The axle slot 504 is open-ended in the proximal direction, which may prove advantageous in allowing the blades 210, 212 to move distally away from the first axle 404*a* as the blades 210, 212 are actuated to the open position.

As also illustrated in FIGS. 5A-5B, the actuation pulleys 406*a,b* are exploded laterally outward from the blades 210, 212 and the first axle 404*a*. Each actuation pulley 406*a,b* defines a pulley aperture 506 sized to receive a corresponding end of the first axle 404*a*. Moreover, as described above, each flange 412*a,b* may be pivotably mounted to the corresponding (adjacent) actuation pulley 406*a,b*, respectively, by receiving a corresponding actuation boss 416 in the associated flange aperture 414. Each actuation boss 416 is located eccentric to the corresponding pulley aperture 506 and otherwise off-center from the first pivot axis $P_1$. The off-center position of the actuation boss 416 will cause the blades 210, 212 to move away from and toward the first axle 404*a* as the actuation pulleys 406*a,b* are actuated (rotated) to open and close the blades 210, 212.

More specifically, once the blades 210, 212 are properly mounted to the corresponding actuation pulley 406*a,b*, rotation (actuation) of the actuation pulleys 406*a,b* will cause the blades 210, 212 to pivot about the third pivot axis $P_3$ and thereby open or close, rotate in tandem about the first pivot axis $P_1$, or a combination of the foregoing. Since the third pivot axis $P_3$ is located distal to the first pivot axis $P_1$, and the actuation bosses 416 are located off-center from the first pivot axis $P_1$, the blades 210, 212 will translate distally or proximally relative to the wrist 206 as the blades 210, 212 open and close.

The blades 210, 212 are highly-utilized during many surgical procedures, and the cutting edges of the blades 210, 212 may dull over time, which can affect the proficiency of the end effector 204. Moreover, in embodiments where the blades 210, 212 are electrified (e.g., monopolar blades), the cutting edge of the blades 210, 212 may further degrade due to monopolar energy employed during procedures. Consequently, the end effector 204 may be designed to be used for only a predetermined number of procedures, and once the predetermined number of procedures is reached, the operator (e.g., a nurse, a doctor, etc.) may be unable to continue using the end effector 204.

According to embodiments of the present disclosure, the blades 210, 212 can be easily and quickly replaced once dulled, thereby extending the useful life of the end effector 204. As described herein, the blades 210, 212 can be replaced by rotating (actuating) the actuation pulleys 406*a,b* until the actuation bosses 416 are positioned in an over-centered position, i.e., where the actuation bosses 416 are arranged (positioned) distal to the first pivot axis $P_1$. Positioning the actuation bosses 416 in the over-centered position exposes the actuation bosses 416, thereby allowing a user (e.g., a service technician, a bedside nurse, a surgeon, etc.) to quickly remove the blades 210, 212 from the actuation pulleys 406*a,b* and install new blades. Once the new blades are properly installed, the actuation pulleys 406*a,b* can again be rotated actuated) until the actuation bosses 416 are arranged (positioned) proximal to the first pivot axis $P_1$.

Figure 6:
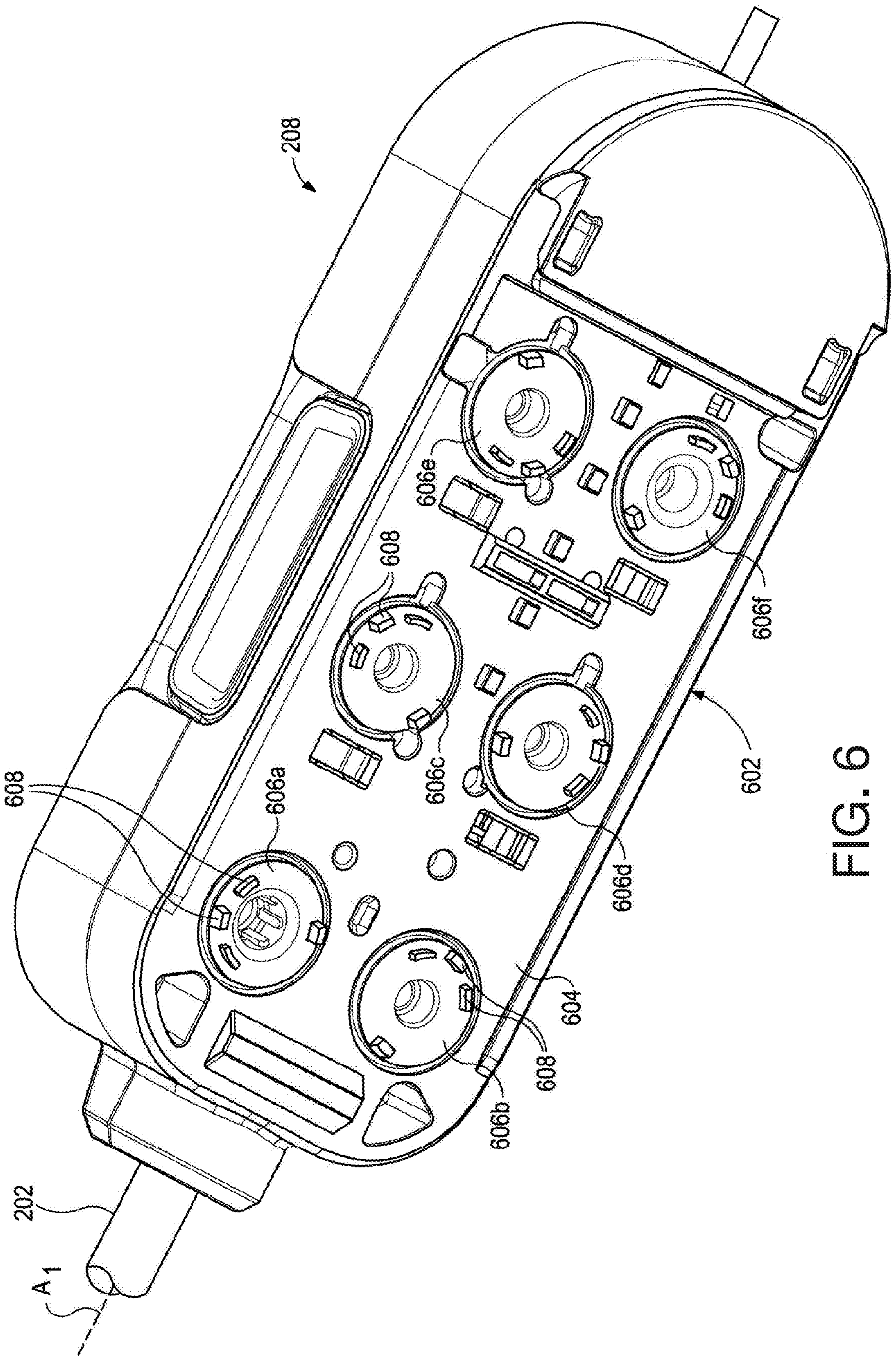
FIG. 6 is a bottom view of the drive housing of FIG. 2, according to one or more embodiments.

FIG. 6 is a bottom view of the drive housing 208 of FIG. 1, according to one or more embodiments. As illustrated, the drive housing 208 may include a tool mounting portion 602 used to operatively couple the drive housing 208 to a tool driver of a robotic manipulator. The tool mounting portion 602 may releasably couple the drive housing 208 to a tool driver in a variety of ways, such as by clamping thereto, clipping thereto, or slidably mating therewith. In some embodiments, the tool mounting portion 602 may include an array of electrical connecting pins, which may be coupled to an electrical connection on the mounting surface of the tool driver. While the tool mounting portion 602 is described herein with reference to mechanical, electrical, and magnetic coupling elements, it should be understood that a wide variety of telemetry modalities might be used, including infrared, inductive coupling, or the like.

The tool mounting portion 602 includes and otherwise provides an interface 604 configured to mechanically, magnetically, and/or electrically couple the drive housing 208 to the tool driver. As illustrated, the interface 604 includes and supports a plurality of drive inputs, shown as drive inputs 606*a*, 606*b*, 606*c*, 606*d*, 606*e*, and 606*f*. Each drive input 606*a-f* comprises a rotatable disc configured to align with and couple to a corresponding actuator or "drive output" of a tool driver, such that rotation (actuation) of a given drive output drives (rotates) a corresponding one of the drive inputs 606*a-f*. Each drive input 606*a-f* may provide or define one or more surface features 608 configured to align with mating surface features provided on the corresponding drive output. The surface features 608 can include, for example, various protrusions and/or indentations that facilitate a mating engagement. In some embodiments, some or all of the drive inputs 606*a-f* may include one surface feature 608 that is positioned closer to an axis of rotation of the associated drive input 606*a-f* than the other surface feature(s) 608. This may help to ensure positive angular alignment of each drive input 606*a-f.*

In some embodiments, actuation of the first drive input 606*a* may be configured to control rotation of the shaft 202 about its longitudinal axis $A_1$. The shaft 202 may be rotated clockwise or counter-clockwise depending on the rotational actuation of the first drive input 606*a*. In some embodiments, actuation of the second, third, fourth, and fifth drive inputs 606*b-e* may be configured to operate movement (axial translation) of the drive cables 418 (FIG. 4), which results in the articulation of the wrist 206 (FIGS. 4 and 5A-5B) and/or operation of the end effector 204 (FIGS. 4 and 5A-5B), such as opening or closing the blades (FIGS. 4 and 5A-5B). Actuation of the sixth drive input 606*f* may cause another operation to be performed in the drive housing 208. Each of the drive inputs 606*a-f* may be actuated based on user inputs communicated to the tool driver coupled to the interface 604, and the user inputs may be received via a computer system incorporated into the robotic surgical system.

Figure 7:
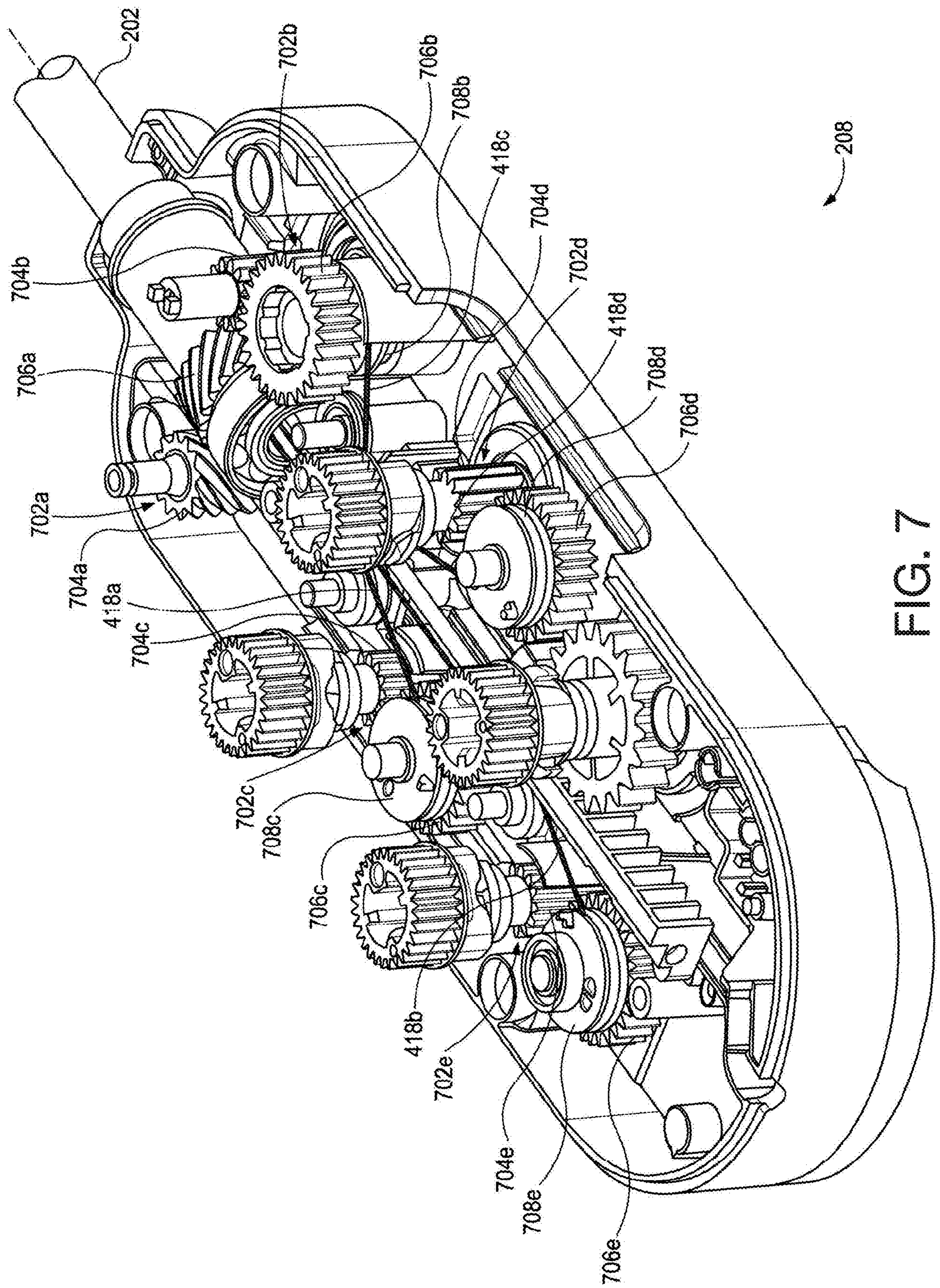
FIG. 7 is an exposed isometric view of the interior of the drive housing of FIG. 2, according to one or more embodiments.

FIG. 7 is an exposed isometric view of the interior of the drive housing 208, according to one or more embodiments. Several component parts that may be otherwise contained within the drive housing 208 are not shown in FIG. 7 to enable discussion of the depicted component parts. As illustrated, the drive housing 208 houses and otherwise contains a plurality of capstan assemblies operable to operate the surgical tool 200 (FIG. 2). In particular, a first capstan assembly 702*a* is contained (housed) within the drive housing 208 and may include a drive gear 704*a* operatively coupled to or extending from the first drive input 606*a* (FIG. 6) such that actuation of the first drive input 606*a* results in rotation of the drive gear 704*a*. The drive gear 704*a* comprises a worm gear configured to mesh and interact with a driven gear 706*a* secured within the drive housing 208 and operatively coupled to the shaft 202 such that rotation of the driven gear 706*a* correspondingly rotates the shaft 202. Accordingly, actuation of the first capstan assembly 702*a*, via actuation of the first drive input 606*a*, will drive the driven gear 706*a* and thereby control rotation of the elongate shaft 202 about the longitudinal axis $A_1$.

The drive housing 208 further contains or houses second, third, fourth, and fifth capstan assemblies 702*b*, 702*c*, 702*d*, and 702*e*, alternately referred to as "drive cable" capstan assemblies since they are operable to actuate the drive cables 418, shown in FIG. 7 as a first drive cable 418*a*, a second drive cable 418*b*, a third drive cable 418*c*, and a fourth drive cable 418*d*. In the illustrated embodiment, the second capstan assembly 702*b* is actuated through operation (rotation) of the second drive input 606*b* (FIG. 6), the third capstan assembly 702*c* is actuated through operation (rotation) of the third drive input 606*c* (FIG. 6), the fourth capstan assembly 702*d* is actuated through operation (rotation) of the fourth drive input 606*d* (FIG. 6), and the fifth capstan assembly 702*e* is actuated through operation (rotation) of the fifth drive input 606*e* (FIG. 6).

As illustrated, each capstan assembly 702*b-e* includes a drive gear 704*b*, 704*c*, 704*d*, and 704*e* that is coupled to or extends from the corresponding drive input 606*b-e*, respectively, such that actuation (rotation) of a given drive input 606*b-e* correspondingly rotates the associated drive gear 704*b-e*, respectively. Each drive gear 704*b-e* is positioned to mesh and interact with a corresponding driven gear 706*b*, 706*c*, 706*d*, and 706*e* rotatably mounted within the drive housing 208. Each driven gear 706*b-e* includes or is otherwise coupled to a corresponding cable pulley 708*b*, 708*c*, 708*d*, and 708*e*, and each cable pulley 708*b-e* is configured to be operatively coupled to (e.g., has wrapped there around, at least partially) a corresponding one of the drive cables 418*a-d*. In the illustrated embodiment, the first drive cable 418*a* terminates at cable pulley 708*c*, which is ultimately driven by actuation of the third capstan assembly 702*c*, the second drive cable 418*b* terminates at cable pulley 708*e*, which is ultimately driven by actuation of the fifth capstan assembly 702*e*, the third drive cable 418*c* terminates at cable pulley 708*b*, which is ultimately driven by actuation of the second capstan assembly 702*b*, and the fourth drive cable 418*d* terminates at cable pulley 708*d*, which is ultimately driven by actuation of the fourth capstan assembly 702*d.*

Accordingly, actuation of the third capstan assembly 702*c* (via operation of the third drive input 606*c* of FIG. 6) will correspondingly control movement of the first drive cable 418*a*; actuation of the fifth capstan assembly 702*e* (via operation of the fifth drive input 606*e* of FIG. 6) will correspondingly control movement of the second drive cable 418*b*; actuation of the second capstan assembly 702*b* (via operation of the second drive input 606*b* of FIG. 6) will correspondingly control movement of the third drive cable 418*c*; and actuation of the fourth capstan assembly 702*d* (via operation of the fourth drive input 606*d* of FIG. 6) will correspondingly control movement of the fourth drive cable 418*d.*

Figure 8C:
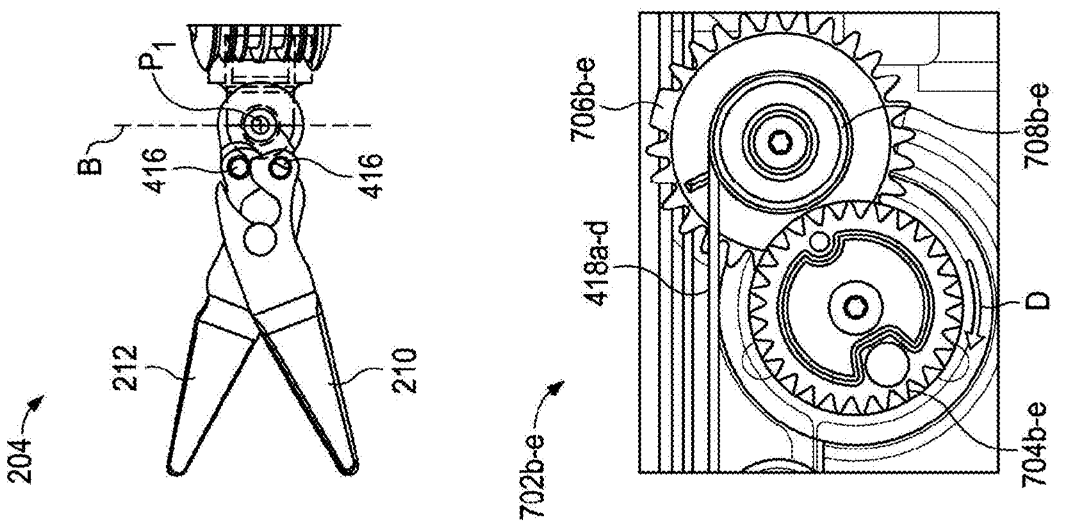
FIGS. 8A, 8B and 8C depict example operation of a given capstan assembly to operate the blades of the end effector, according to one or more embodiments.
Figure 8B:
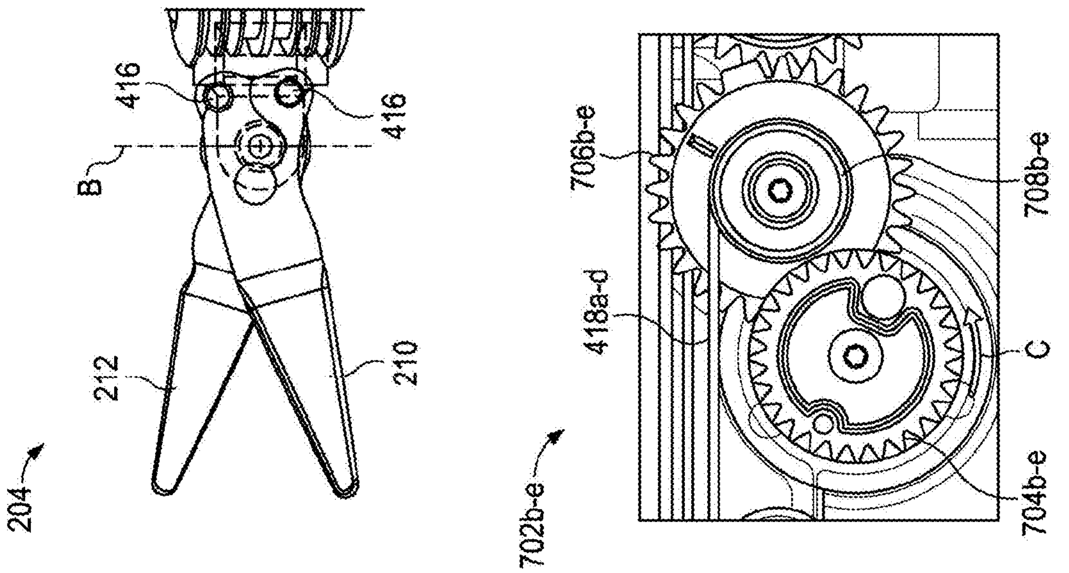
Figure 8A:
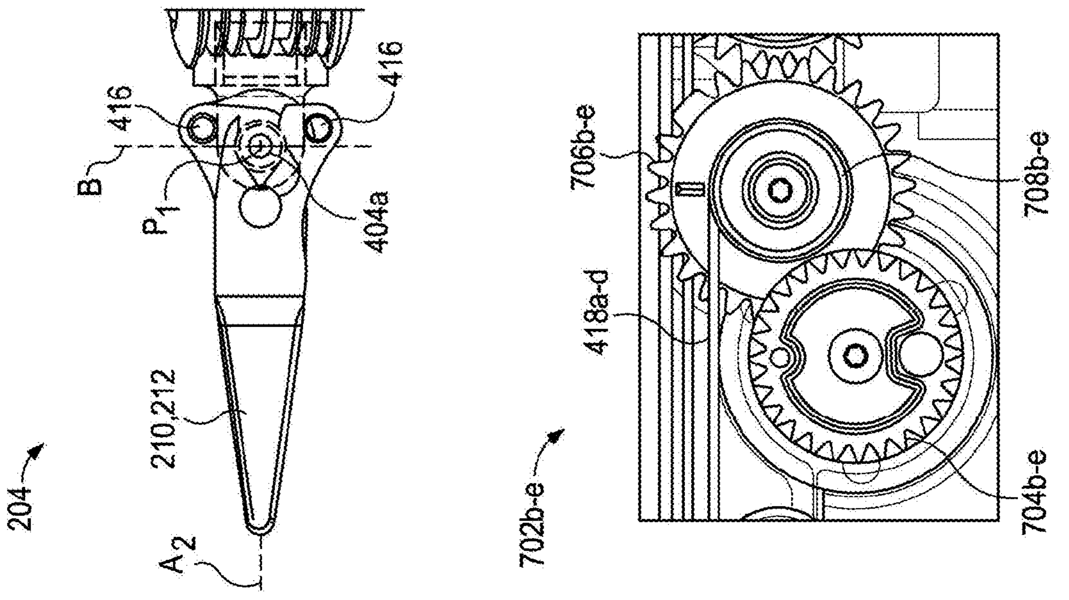

FIGS. 8A-8C depict example operation of a given capstan assembly 702*b-e* to operate the blades 210, 212 of the end effector 204, according to one or more embodiments. FIGS. 8A-8C each include an upper image, which depicts operational configurations of the end effector 204, and a lower image, which depicts corresponding operational orientations of the capstan assembly 702*b-e* (lower image). While only one capstan assembly 702*b-e* is depicted in FIGS. 8A-8C, it will be appreciated that the depicted capstan assembly 702*b-e* may represent any and all of the capstan assemblies 702*b-e* described above with reference to FIG. 7. As discussed above, the capstan assembly 702*b-e* includes the drive gear 704*b-e*, which is arranged to drive a corresponding driven gear 706*b-e*. Moreover, each driven gear 706*b-e* includes a corresponding cable pulley 708*b-e* about which a corresponding one of the drive cables 418*a-d* is wrapped. Accordingly, actuation of the capstan assembly 702*b-e* correspondingly actuates the associated drive cable 418*a-d* to manipulate the orientation or operational configuration of the end effector 204.

FIG. 8A depicts the blades 210, 212 in a first or "closed" position, FIG. 8B depicts the blades 210, 212 moved to a second or "open" position, and FIG. 8C depicts the blades 210, 212 moved to a third or "over-centered" position. To transition the blades 210, 212 between the closed, open, and over-centered positions, each capstan assembly 702*b-e* may be selectively actuated in unison to actuate corresponding drive cables 418*a-d* and thereby cause an associated actuation pulley 406*a,b* (FIGS. 4 and 5A-5B) to rotate, which causes the blades 210, 212 to move.

Referring first to FIG. 8A, the drive gear 704*b-e* is shown oriented in a first angular position and, as a result of such orientation, the blades 210, 212 are closed. In particular, when the drive gear 704*b-e* is in the first angular position, the actuation pulleys 406*a,b* (FIGS. 4 and 5A-5B) may be oriented such that the corresponding actuation bosses 416 are located proximal to a centerline B of the first axle 404*a* (i.e., to the right of the centerline B in FIG. 8A), thereby closing the blades 210, 212. The centerline B is a plane that passes through the first pivot axis $P_1$ of the first axle 404*a*, but is perpendicular to the longitudinal axis $A_2$ of the end effector 204.

In FIG. 8B, the blades 210, 212 have transitioned from the closed position to an open position. To accomplish this, the drive gear 704*b-e* may be rotated in a first angular direction, as shown by the arrow C, and stop at a second angular position. Rotating the drive gear 704*b-e* in the first angular direction C and to the second angular position correspondingly rotates the driven gear 706*b-e* and thereby actuates the associated drive cable 418*a-d*. As the drive cable 418*a-d* is actuated (e.g., moved longitudinally), the corresponding actuation pulley 406*a,b* (FIGS. 4 and 5A-5B) will be actuated (rotated) to move the position (orientation) of the actuation bosses 416, thereby opening the blades 210, 212. As illustrated, when the blades 210, 212 are moved to the open position, the actuation bosses 416 are correspondingly moved further from the centerline B in the proximal direction, and the blades 210, 212 are correspondingly drawn proximally as the actuation bosses 416 move proximally.

During normal operation of the end effector 204, the blades 210, 212 can be moved between the closed and open positions multiple times, and the orientation of the actuation bosses 416 correspondingly moves. During normal operation, however, the actuation bosses 416 are prohibited from crossing the centerline B, which would transition the blades 210, 212 to the over-centered position and thereby make the end effector 204 unstable. In some embodiments, maintaining the actuation bosses 416 proximal to the centerline B can be accomplished by selectively actuating the capstan assemblies 702*b-e* such that the drive cables 418*a-d* are prevented from rotating the actuation bosses 416 past the centerline B. In such embodiments, the robotic manipulator tool driver where the drive housing 208 (FIGS. 2, 6, and 7) is mounted may be programmed and otherwise configured to operate the capstan assemblies 702*b-e* accordingly, and thus algorithmically prevent an over-centered condition. In other embodiments, however, and as described in more detail below, the drive housing 208 may include a rotation limiter system (not shown) that physically prevents one or more of the capstan assemblies 702*b-e* from operating (rotating) such that the actuation bosses 416 are transitioned past the centerline B.

In FIG. 8C, the blades 210, 212 are transitioned to the over-centered position. To accomplish this, the drive gear 704*b-e* may be rotated in a second angular direction opposite the first angular direction, as shown by the arrow D, and stop at a third angular position. In some embodiments, the robotic manipulator tool driver where the drive housing 208 (FIGS. 2, 6, and 7) is mounted may be programmed and otherwise configured to operate (rotate) the capstan assemblies 702*b-e* to achieve the third angular position. In other embodiments, however, the drive gear 704*b-e* may be manually rotated in the second angular direction and to the third angular position using a separate fixture device (not shown). In such embodiments, the drive housing 208 must first be detached from the tool driver and mounted to the separate fixture device. In some applications, mounting the drive housing 208 to the fixture device automatically releases (unlocks) the drive inputs 606*a-d* (FIG. 6), thereby allowing a user to manually rotate the drive inputs 606*a-d* in the second angular direction until the blades 210, 212 are transitioned to the over-centered position. In other embodiments, the fixture device may be automated and otherwise robotically operated. In such embodiments, the fixture device may be programmed to rotate the drive inputs 606*a-d* until drive gear 704*b-e* is rotated to the third angular position and the blades 210, 212 are transitioned to the over-centered position.

Transitioning the blades 210, 212 to the over-centered position causes the actuation bosses 416 to bypass (traverse) the centerline B in the distal direction and otherwise be oriented distal to the first pivot axis $P_1$. Orienting the actuation bosses 416 distal to the first pivot axis $P_1$ correspondingly moves the blades 210, 212 distally and thereby exposes the actuation bosses 416. With the actuation bosses 416 exposed, a user (e.g., a sterilization technician, bedside assist, a nurse, a surgeon, etc.) may be able to manually remove the blades 210, 212 from the corresponding actuation pulleys 406*a,b* (FIGS. 4 and 5A-5B). Once the blades 210, 212 are removed, a new set of blades can then be installed on the actuation pulleys 406*a,b*, following which the blades 210, 212 can be transitioned back to the open or closed positions, where the actuation bosses 416 are oriented proximal to the centerline B and prevented from removal. The end effector 204 may then be ready for future use.

Figure 9B:
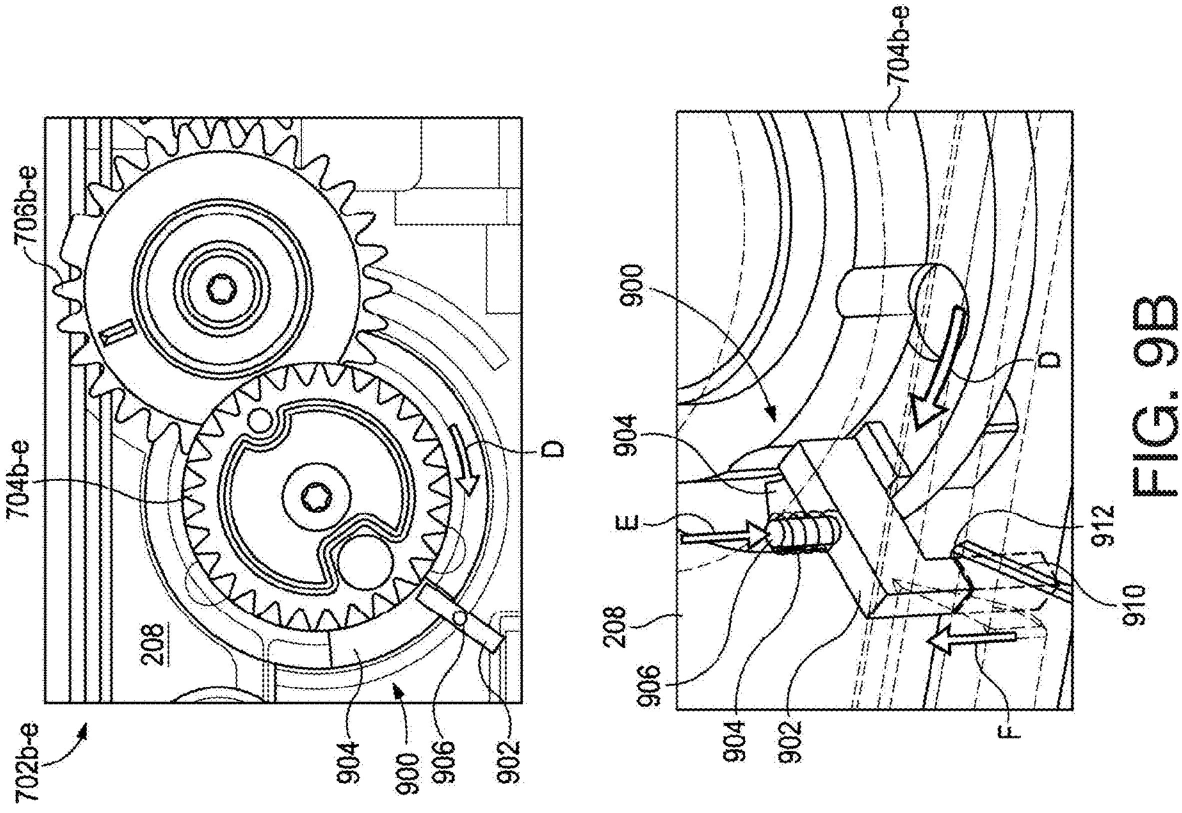
FIGS. 9A and 9B depict an example rotation limiter system, according to one or more embodiments of the present disclosure.
Figure 9A:
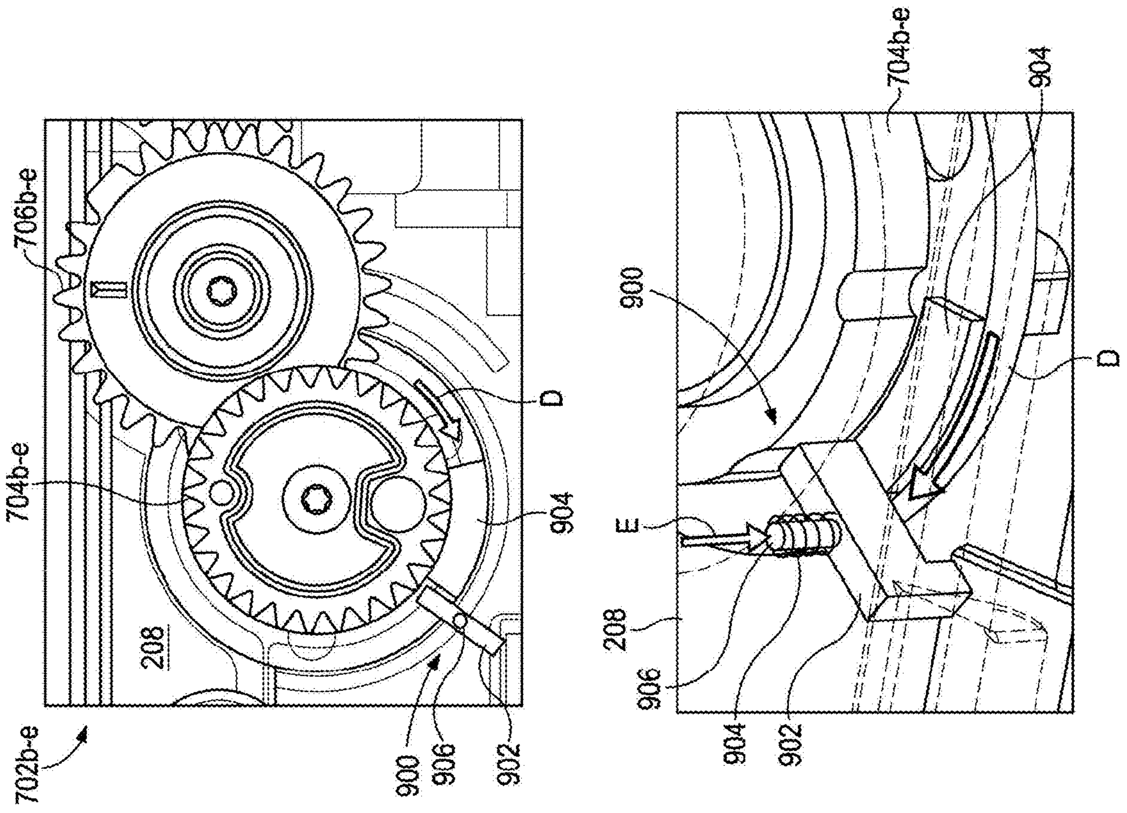

FIGS. 9A and 9B depict an example rotation limiter system 900 that may be used in conjunction with a given capstan assembly 702*b-e*, according to one or more embodiments of the present disclosure. FIGS. 9A-9B each provide an upper image, which depicts a top view of a given capstan assembly 702*b-e* and the rotation limiter system 900, and a lower image, which depicts a partial isometric view of the given capstan assembly 702*b-e* and the rotation limiter system 900. While only one capstan assembly 702*b-e* is depicted in FIGS. 9A-9BC, it will be appreciated that the depicted capstan assembly 702*b-e* may represent any and all of the capstan assemblies 702*b-e* described above with reference to FIG. 7. As discussed above, the capstan assembly 702*b-e* includes the drive gear 704*b-e*, which is arranged to drive a corresponding driven gear 706*b-e*.

The rotation limiter system 900 may be configured to physically prevent the capstan assembly 702*b-e* from rotating in the second angular direction D and to the third angular position. In particular, the rotation limiter system 900 physically prevents the drive gear 704*b-e* from rotating past a predetermined angular position corresponding to a point where the actuation bosses 416 (FIGS. 8A-8C) traverse the centerline B (FIGS. 8A-8C) and thereby move the blades 210, 212 (FIGS. 8A-8C) to the over-centered position, as shown in FIG. 8C.

As illustrated, the rotation limiter system 900 includes a gate 902 mounted within the drive housing 208, and an engagement member 904 engageable with the gate 902. The gate 902 may be vertically mounted within the drive housing 208 and able to move up and down between a first or "blocking" position, as shown in FIG. 9A, and a second or "unobstructed" position, as shown in FIG. 9B. In some embodiments, a spring 906 may be compliantly mounted to the gate 902 and configured to naturally bias the gate 902 downward and to the blocking position, as shown by the arrow E. In at least one embodiment, the gate 902 may define a shaft 908 and the spring 906 may be mounted about the shaft 908. In such embodiments, one end of the spring 906 may engage the gate 902, and the other end of the spring 906 may engage a surface of the drive housing 208.

The engagement member 904 may be coupled to the drive gear 704*b-e* such rotation of the drive gear 704*b-e* correspondingly rotates the engagement member 904 in the same angular direction. In the illustrated embodiment, the engagement member 904 comprises a radial shoulder or ledge that extends radially outward from the drive gear 704*b-e* and is engageable with the gate 902. More specifically, when the gate 902 is in the blocking position, as shown in FIG. 9A, rotation of the drive gear 704*b-e* in the second angular direction D may be stopped once the engagement member 904 laterally engages the gate 902. Physical engagement between the gate 902 and the engagement member 904 prevents the drive gear 704*b-e* from rotating to the third angular position and otherwise to a point where the actuation bosses 416 (FIGS. 8A-8C) traverse the centerline B (FIGS. 8A-8C) and thereby move the blades 210, 212 (FIGS. 8A-8C) to the over-centered position, as shown in FIG. 8C.

When it is desired to move the blades 210, 212 (FIGS. 8A-8C) to the over-centered position, however, such as when it is desired to remove and replace the blades 210, 212, the gate 902 may be transitioned to the unobstructed position, as shown in FIG. 9B. In some embodiments, this can be accomplished by inserting a release pin 910 (shown in dashed lines) into an aperture 912 defined in the bottom of the drive housing 208 and engaging the gate 902. Once engaged with the gate 902, the release pin 910 may then be pushed upward, as shown by the arrow F, which causes the gate 902 to move in the same direction and out of lateral engagement with the engagement member 904. Moving the gate 902 upward F also compresses the spring 904, thereby building spring force, and moving the releaser pin 910 out of engagement with the gate 902 will allow the spring force to release and move the gate 902 back to the blocking position.

Once the gate 902 is moved out of lateral engagement with the engagement member 904, the drive gear 704*b-e* may then be actuated to rotate in the second angular direction D, thereby allowing the engagement member 904 to angularly bypass the gate 902. The drive gear 704*b-e* may be rotated in the second angular direction D to the third angular position and otherwise until the actuation bosses 416 (FIGS. 8A-8C) traverse the centerline B (FIGS. 8A-8C) and thereby move the blades 210, 212 (FIGS. 8A-8C) to the over-centered position, as shown in FIG. 8C.

In some embodiments, a user (e.g., a sterilization technician, bedside assist, a nurse, a surgeon, etc.) may manually insert the release pin 910 into the aperture 912 of the drive housing 208 and thereby transition the gate 902 to the unobstructed position. In other embodiments, however, the drive housing 208 may be detached from the robotic manipulator tool driver and subsequently mounted to a separate fixture device (not shown), as described above. In such embodiments, the release pin 910 may form an integral part of the fixture device such that mounting the drive housing 208 to the fixture device may automatically transition the gate 902 to the unobstructed position.

Figure 10:
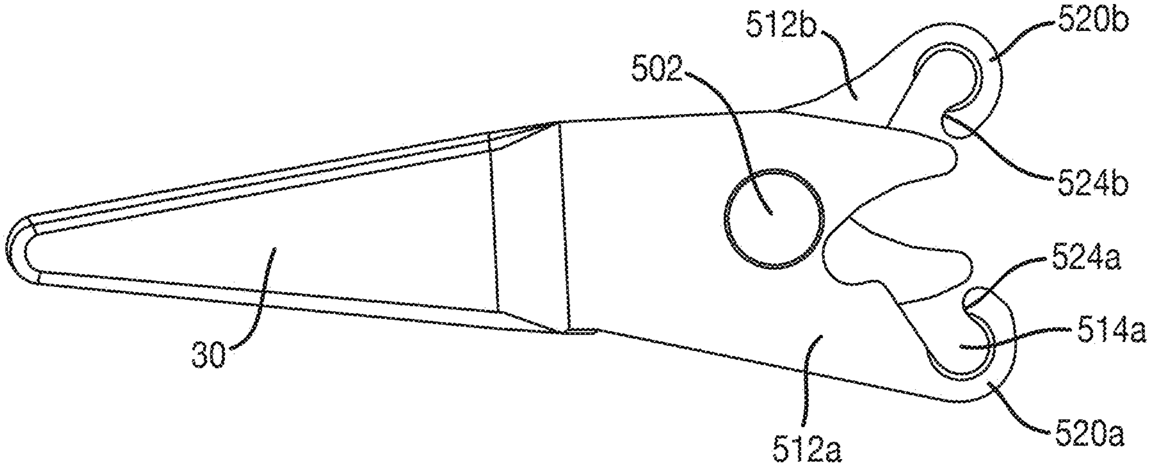
FIG. 10 is a side view of a component of an end effector that may incorporate some or all of the principles of the present disclosure.

FIG. 10 shows an alternate blade geometry for engaging with the actuation bosses 416 on actuation pulleys 406. Blades 310 and 312 rotate about a center pin 502. Blades 310 and 312 have a proximal end and distal end, the distal end contains a sharpened inner edge for cutting. Flanges 512*a* and 512*b* transition between the distal end and proximal end of blades 310 and 312. The proximal end blades 310 and 312 have an attachment feature for removably coupling with an end effector of a surgical instrument.

The attachment feature on the proximal end of blades 310 and 312 can vary in geometry. Blades 210 and 212, described earlier, depict an eclosed flange aperture 414 for receiving actuation bosses 416. However, blades 310 and 312 have an open flange aperture 514*a* and 514*b* respectively that are not fully enclosed 360 degrees around the circumference. Flange apertures 514*a* and 514*b* are formed by flange locks 520*a* and 520*b* that extend from flanges 512*a* and 512*b*. Flange locks 520*a* and 520*b* curl towards longitudinal axis $A_2$ (not shown) thus forming a hook like shape that terminates at terminal ends 524*a* and 524*b*. The opening left between terminal end (524*a*, 524*b*) and the respective flange from which it originated (512*a*, 512*b*) must be large enough to allow the actuation boss 416 to freely pass through into the flange aperture (514*a*, 514*b*). However, in another embodiment, terminal ends 524*a* and 524*b* or flanges 512*a* and 512*b*, or both, may contain a detent that makes the gap between terminal end (524*a*, 524*b*) and the respective flange from which it originated (512*a*, 512*b*) smaller than the diameter of the actuation boss 416 thus creating an interference fit that must be overcome by an increased force prior to removal or insertion of the actuation bosses 416 in flange apertures 514*a* and 514*b*.

Figure 11:
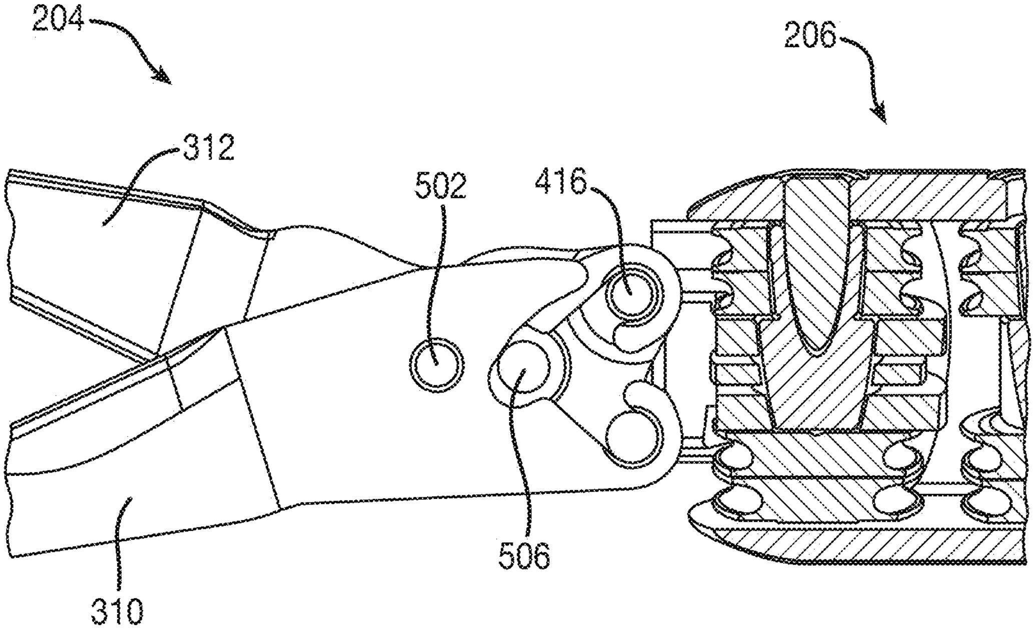
FIG. 11 is a side view of an end effector according to one or more embodiments.

FIG. 11 shows blades 310 and 312 engaged with actuation bosses 416 and in an in use or ready for use condition.

Figure 12A:
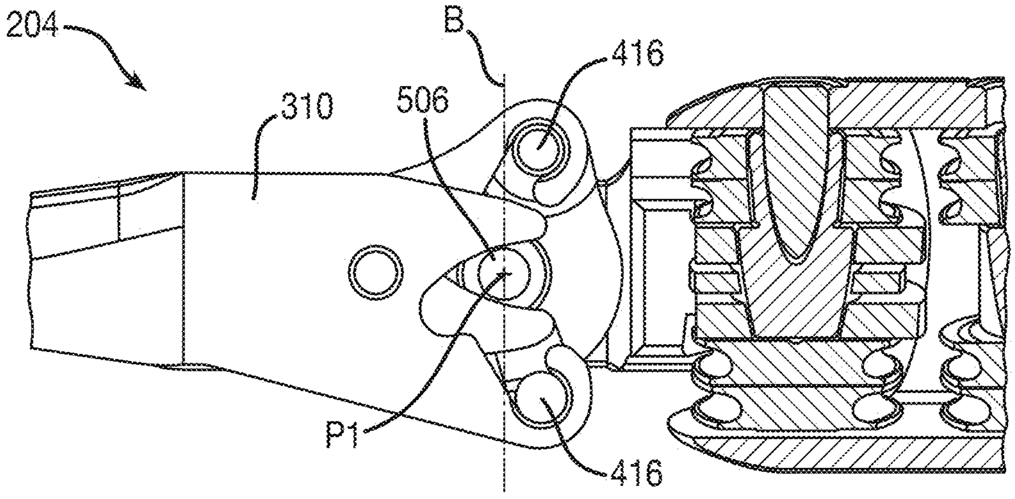
Figure 12B:
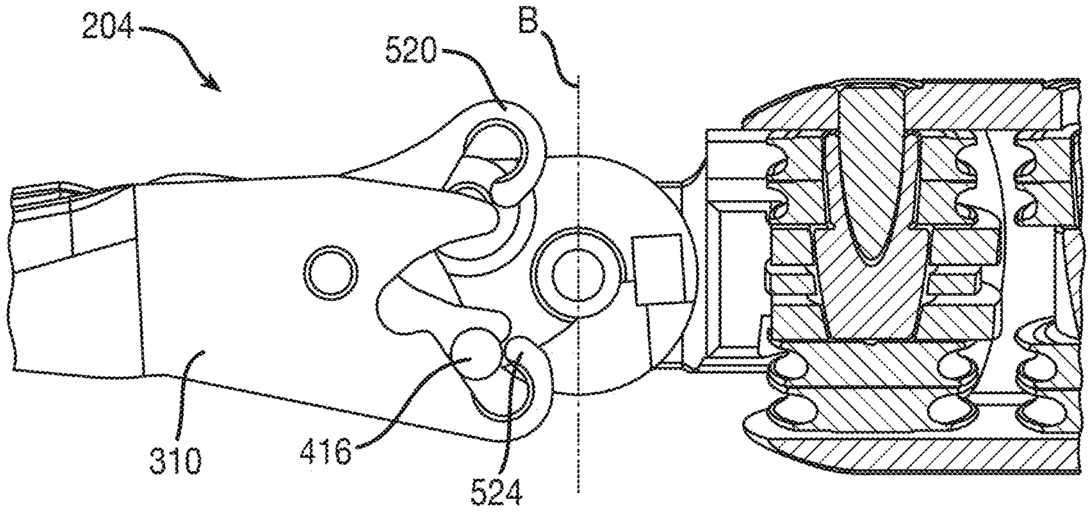
Figure 12C:
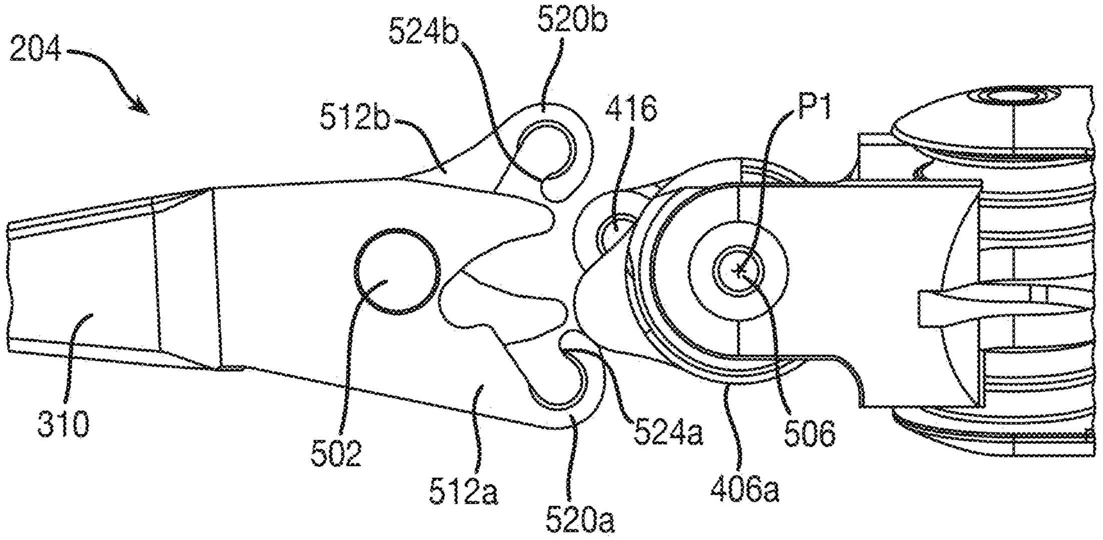

FIGS. 12A-12C show a sequence of illustrations starting with the end effector in a first or "closed" position, a second or "engaged over-centered" position, and lastly a third position or "unengaged over-center" position. In the first position, shown in FIG. 12A, blades 310 and 312 are closed and actuation bosses 416 are proximal to centerline B. When it is desired to replace blades 310 and 312 actuation pulleys 406 may be operated beyond the "closed" position until the actuation bosses 416 on actuation pulleys 416 cross beyond the centerline B to the distal or over-center position relative to centerline B as shown. As shown in FIG. 12B, blades 310 and 312 remain in the "closed" position, however, actuation bosses 416 are now distal to centerline B or in the "over-center" position. As actuation bosses 416 continue to proceed further into the over-centered position the actuation bosses begin to move out of the respective flange apertures 514*a* and 514*b* and disengage from the flange locks 520*a* and 520*b*. FIG. 12C shows a completely disengaged state where actuation pulleys 406*a* and 406*b* have rotated actuation bosses 416 past the terminal ends 524*a* and 524*b* of flange locks 520*a* and 520*b*. At this point blades 310 and 312 are free to be removed from end effector 204.

To install a new set of blades 310 and 312 on end effector 204, the sequence shown in FIGS. 12A-12C would be reversed. Old blades 310 and 312 would be simply discarded and replaced with new blades. Another option is that the old blades 310 and 312 would be removed and reprocessed (such as resharpening the cutting edge) and then reinstalled onto end effector 204.

Embodiments disclosed herein include:

A. A surgical tool includes a drive housing, an elongate shaft extending distally from the drive housing, a wrist arranged at a distal end of the shaft and including a distal clevis, an axle mounted to the distal clevis, and first and second actuation pulleys rotatably mounted to the axle and rotatable about a pivot axis extending through the axle, each actuation pulley providing an actuation boss eccentric to the pivot axis, and an end effector operatively coupled to the wrist. The end effector includes a first blade with a first locking portion and a first terminal end defining a first gap between the first blade and the first terminal end, wherein the first blade is pivotably coupled to the actuation boss of the first actuation pulley and a second blade with a second locking portion and a second terminal end defining a second gap between the second blade and the second terminal end, the second blade rotatably coupled to the first blade at a center pin and pivotably coupled to the actuation boss of the second actuation pulley, wherein the first and second blades are movable between open and closed positions by rotating the first and second actuation pulleys such that the actuation boss of each actuation pulley remains proximal to a centerline of the axle, wherein the first and second blades are movable to an over-centered position by rotating the first and second actuation pulleys such that the actuation boss of each actuation pulley is located distal to the centerline, and wherein moving the first and second blades to the over-centered position exposes the actuation boss of each actuation pulley, thereby allowing the first and second blades to be removed.

B. A method of replacing first and second blades of an end effector, the method including providing a surgical tool that includes the end effector and further includes a drive housing, an elongate shaft extending distally from the drive housing, and a wrist arranged at a distal end of the shaft and including a distal clevis, an axle mounted to the distal clevis, and first and second actuation pulleys rotatably mounted to the axle and rotatable about a pivot axis extending through the axle, each actuation pulley providing an actuation boss eccentric to the pivot axis, and a first blade with a first locking portion and a first terminal end defining a first gap between the first blade and the first terminal end, wherein the first blade is pivotably coupled to the actuation boss of the first actuation pulley and a second blade with a second locking portion and a second terminal end defining a second gap between the second blade and the second terminal end, wherein the second blade is rotatably coupled to the first blade at a center pin and pivotably coupled to the actuation boss of the second actuation pulley. The method further including the steps of moving the first and second blades to an over-centered position by rotating the first and second actuation pulleys such that the actuation boss of each actuation pulley is located distal to a centerline of the axle, exposing the actuation boss of each actuation pulley once the first and second blades are moved to the over-centered position, and removing the first and second blades from the first and second actuation pulleys with the first and second blades in the over-centered position.

C. An end effector for a surgical tool includes a wrist including a distal clevis, an axle mounted to the distal clevis, and first and second actuation pulleys rotatably mounted to the axle and rotatable about a pivot axis extending through the axle, each actuation pulley providing an actuation boss eccentric to the pivot axis, a first blade with a first locking portion and a first terminal end defining a first gap between the first blade and the first terminal end, wherein the first blade is pivotably coupled to the actuation boss of the first actuation pulley and a second blade with a second locking portion and a second terminal end defining a second gap between the second blade and the second terminal end, the second blade rotatably coupled to the first blade at a center pin and pivotably coupled to the actuation boss of the second actuation pulley, wherein the first and second blades are movable between open and closed positions by rotating the first and second actuation pulleys such that the actuation boss of each actuation pulley remains proximal to a centerline of the axle, wherein the first and second blades are movable to an over-centered position by rotating the first and second actuation pulleys such that the actuation boss of each actuation pulley is located distal to the centerline, and wherein moving the first and second blades to the over-centered position exposes the actuation boss of each actuation pulley, thereby allowing the first and second blades to be removed.

Each of embodiments A, B, and C may have one or more of the following additional elements in any combination: Element 1: wherein the pivot axis comprises a first pivot axis, and a second pivot axis extends through the center pin, and wherein the second pivot axis extends parallel to the first pivot axis and is located distal to the first pivot axis. Element 2: wherein the first blade includes a first proximally extending flange adjacent the first locking portion, and the second blade includes a second proximally extending flange adjacent the second locking portion. Element 3: wherein the first blade has one or more detents that protrude into the first gap. Element 4: wherein the second blade has one or more detents that protrudes into the second gap. Element 5: wherein the centerline of the axle comprises a plane that passes through the pivot axis and is perpendicular to a longitudinal axis of the end effector. Element 6: further comprising a plurality of capstan assemblies arranged within the drive housing, and a plurality of drive cables operatively coupled to and extending from the plurality of capstan assemblies, a first pair of the plurality of drive cables terminating at the first actuation pulley and a second pair of the plurality of drive cables terminating at the second actuation pulley, wherein selective actuation of the plurality of capstan assemblies causes the first and second actuation pulleys to rotate and thereby move the first and second blades between the open and closed positions, and further to the over-centered position. Element 7: wherein each capstan assembly includes a drive gear, and a driven gear arranged to intermesh with the drive gear and including a cable pulley configured to receive an end of a corresponding one of the plurality of drive cables, wherein rotating the drive gear in a first angular direction from a first angular position to a second angular position transitions the first and second blades from the closed position to the open position, and wherein rotating the drive gear in a second angular direction opposite the first angular direction from the first angular position to a third angular position transitions the first and second blades to the over-centered position. Element 8: further comprising a rotation limiter system operable to physically prevent the drive gear from rotating in the second angular direction to the third angular position. Element 9: wherein the rotation limiter system comprises a gate movably mounted within the drive housing, and an engagement member coupled to the drive gear such rotation of the drive gear correspondingly rotates the engagement member in a same angular direction, wherein the gate is movable between a blocking position, where the gate prevents the engagement member from angularly bypassing the gate, and an unobstructed position, where the gate is moved to allow the drive gear to rotate to the third angular position. Element 10: wherein the rotation limiter system further includes a spring compliantly mounted to the gate to naturally bias the gate to the blocking position, and a release pin receivable within an aperture defined in the drive housing and engageable with the gate, wherein advancing the release pin into the aperture and engaging the gate transitions the gate from the blocking position to the unobstructed position.

Element 11: further comprising installing first and second new blades on the first and second actuation pulleys, and transitioning the first and second new blades from the over-centered position by rotating the first and second actuation pulleys such that the actuation boss of each actuation pulley is located proximal to the centerline. Element 12: further comprising moving the first and second blades between open and closed positions by rotating the first and second actuation pulleys such that the actuation boss of each actuation pulley remains proximal to the centerline. Element 13: wherein the centerline of the axle comprises a plane that passes through the pivot axis and is perpendicular to a longitudinal axis of the end effector. Element 14: wherein the surgical tool further includes a plurality of capstan assemblies arranged within the drive housing, and a plurality of drive cables operatively coupled to and extending from the plurality of capstan assemblies, a first pair of the plurality of drive cables terminating at the first actuation pulley and a second pair of the plurality of drive cables terminating at the second actuation pulley, the method further comprising actuating the plurality of capstan assemblies and thereby rotating the first and second actuation pulleys to rotate and thereby move the first and second blades to the over-centered position. Element 15: wherein each capstan assembly includes a drive gear and a driven gear arranged to intermesh with the drive gear, the method further comprising rotating the drive gear in a first angular direction from a first angular position to a second angular position and thereby transitioning the first and second blades from a closed position to an open position, rotating the drive gear in a second angular direction opposite the first angular direction from the first angular position and toward a third angular position, and physically prevent the drive gear from rotating in the second angular direction to the third angular position with a rotation limiter system included in the drive housing. Element 16: wherein the rotation limiter system includes a gate movably mounted within the drive housing and an engagement member coupled to the drive gear, the method further comprising engaging the engagement member against the gate and thereby preventing the drive gear from rotating in the second angular direction to the third angular position, moving the gate from a blocking position, where the gate prevents the engagement member from angularly bypassing the gate, and an unobstructed position, where the gate is moved to allow the drive gear to rotate to the third angular position, and rotating the drive gear to the third angular position and thereby transitioning the first and second blades to the over-centered position. Element 17: wherein the rotation limiter system further includes a spring compliantly mounted to the gate to naturally bias the gate to the blocking position, and a release pin receivable within an aperture defined in the drive housing and engageable with the gate, the method further comprising advancing the release pin into the aperture, and engaging the gate with the release pin and thereby transitioning the gate from the blocking position to the unobstructed position.

Element 18: wherein the first blade includes a first proximally extending flange pivotably coupled to the actuation boss of the first actuation pulley, and the second blade includes a second proximally extending flange pivotably coupled to the actuation boss of the second actuation pulley, and wherein each proximally extending flange defines an open-ended axle slot configured to receive the axle. Element 19: wherein the centerline of the axle comprises a plane that passes through the pivot axis and is perpendicular to a longitudinal axis of the end effector.

By way of non-limiting example, exemplary combinations applicable to A, B, and C include: Element 2 with Element 3; Element 3 with Element 4; Element 4 with Element 5; Element 5 with Element 6; Element 6 with Element 7; Element 7 with Element 8; Element 12 with Element 13; Element 13 with Element 14; and Element 14 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:

a drive housing;

an elongate shaft extending distally from the drive housing;

a wrist arranged at a distal end of the shaft and including a distal clevis, an axle mounted to the distal clevis, and first and second actuation pulleys rotatably mounted to the axle and rotatable about a pivot axis extending through the axle, each actuation pulley providing an actuation boss eccentric to the pivot axis; and an end effector operatively coupled to the wrist and including:

a first blade with a first locking portion and a first terminal end defining a first gap between the first blade and the first terminal end, wherein the first blade is pivotably coupled to the actuation boss of the first actuation pulley; and a second blade with a second locking portion and a second terminal end defining a second gap between the second blade and the second terminal end, wherein the second blade is rotatably coupled to the first blade at a center pin and pivotably coupled to the actuation boss of the second actuation pulley, wherein the first and second blades are movable between open and closed positions by rotating the first and second actuation pulleys such that the actuation boss of each actuation pulley remains proximal to a centerline of the axle, wherein the first and second blades are movable to an over-centered position by rotating the first and second actuation pulleys such that the actuation boss of each actuation pulley is located distal to the centerline, and wherein moving the first and second blades to the over-centered position exposes the actuation boss of each actuation pulley, thereby allowing the first and second blades to be removed.

2. The surgical tool of claim 1, wherein the pivot axis comprises a first pivot axis, and a second pivot axis extends through the center pin, and wherein the second pivot axis extends parallel to the first pivot axis and is located distal to the first pivot axis.

3. The surgical tool of claim 1, wherein the first blade includes a first proximally extending flange adjacent the first locking portion, and the second blade includes a second proximally extending flange adjacent the second locking portion.

4. The surgical tool of claim 1, wherein the first blade has one or more detents that protrude into the first gap.

5. The surgical tool of claim 4, wherein the second blade has one or more detents that protrude into the second gap.

6. The surgical tool of claim 1, wherein the centerline of the axle comprises a plane that passes through the pivot axis and is perpendicular to a longitudinal axis of the end effector.

7. The surgical tool of claim 1, further comprising:

a plurality of capstan assemblies arranged within the drive housing; and a plurality of drive cables operatively coupled to and extending from the plurality of capstan assemblies, a first pair of the plurality of drive cables terminating at the first actuation pulley and a second pair of the plurality of drive cables terminating at the second actuation pulley, wherein selective actuation of the plurality of capstan assemblies causes the first and second actuation pulleys to rotate and thereby move the first and second blades between the open and closed positions, and further to the over-centered position.

8. The surgical tool of claim 7, wherein each capstan assembly includes:

a drive gear; and a driven gear arranged to intermesh with the drive gear and including a cable pulley configured to receive an end of a corresponding one of the plurality of drive cables, wherein rotating the drive gear in a first angular direction from a first angular position to a second angular position transitions the first and second blades from the closed position to the open position, and wherein rotating the drive gear in a second angular direction opposite the first angular direction from the first angular position to a third angular position transitions the first and second blades to the over-centered position.

9. The surgical tool of claim 8, further comprising a rotation limiter system operable to physically prevent the drive gear from rotating in the second angular direction to the third angular position.

10. The surgical tool of claim 9, wherein the rotation limiter system comprises:

a gate movably mounted within the drive housing; and an engagement member coupled to the drive gear such rotation of the drive gear correspondingly rotates the engagement member in a same angular direction, wherein the gate is movable between a blocking position, where the gate prevents the engagement member from angularly bypassing the gate, and an unobstructed position, where the gate is moved to allow the drive gear to rotate to the third angular position.

11. The surgical tool of claim 10, wherein the rotation limiter system further includes:

a spring compliantly mounted to the gate to naturally bias the gate to the blocking position; and a release pin receivable within an aperture defined in the drive housing and engageable with the gate, wherein advancing the release pin into the aperture and engaging the gate transitions the gate from the blocking position to the unobstructed position.

12. A method of replacing first and second blades of an end effector, comprising:

providing a surgical tool that includes the end effector and further includes:

a drive housing;

an elongate shaft extending distally from the drive housing;

a wrist arranged at a distal end of the shaft and including a distal clevis, an axle mounted to the distal clevis, and first and second actuation pulleys rotatably mounted to the axle and rotatable about a pivot axis extending through the axle, each actuation pulley providing an actuation boss eccentric to the pivot axis;

a first blade with a first locking portion and a first terminal end defining a first gap between the first blade and the first terminal end, wherein the first blade is pivotably coupled to the actuation boss of the first actuation pulley; and a second blade with a second locking portion and a second terminal end defining a second gap between the second blade and the second terminal end, wherein the first blade is pivotably coupled to the actuation boss of the first actuation pulley, and the second blade is rotatably coupled to the first blade at a center pin and pivotably coupled to the actuation boss of the second actuation pulley;

moving the first and second blades to an over-centered position by rotating the first and second actuation pulleys such that the actuation boss of each actuation pulley is located distal to a centerline of the axle;

exposing the actuation boss of each actuation pulley once the first and second blades are moved to the over-centered position; and removing the first and second blades from the first and second actuation pulleys with the first and second blades in the over-centered position.

13. The method of claim 10, further comprising:

installing first and second new blades on the first and second actuation pulleys; and transitioning the first and second new blades from the over-centered position by rotating the first and second actuation pulleys such that the actuation boss of each actuation pulley is located proximal to the centerline.

14. The method of claim 10, further comprising moving the first and second blades between open and closed positions by rotating the first and second actuation pulleys such that the actuation boss of each actuation pulley remains proximal to the centerline.

15. The method of claim 10, wherein the centerline of the axle comprises a plane that passes through the pivot axis and is perpendicular to a longitudinal axis of the end effector.

16. The method of claim 10, wherein the surgical tool further includes a plurality of capstan assemblies arranged within the drive housing, and a plurality of drive cables operatively coupled to and extending from the plurality of capstan assemblies, a first pair of the plurality of drive cables terminating at the first actuation pulley and a second pair of the plurality of drive cables terminating at the second actuation pulley, the method further comprising:

actuating the plurality of capstan assemblies and thereby rotating the first and second actuation pulleys to rotate and thereby move the first and second blades to the over-centered position.

17. The method of claim 16, wherein each capstan assembly includes a drive gear and a driven gear arranged to intermesh with the drive gear, the method further comprising:

rotating the drive gear in a first angular direction from a first angular position to a second angular position and thereby transitioning the first and second blades from a closed position to an open position;

rotating the drive gear in a second angular direction opposite the first angular direction from the first angular position and toward a third angular position; and physically prevent the drive gear from rotating in the second angular direction to the third angular position with a rotation limiter system included in the drive housing.

18. The method of claim 17, wherein the rotation limiter system includes a gate movably mounted within the drive housing and an engagement member coupled to the drive gear, the method further comprising:

engaging the engagement member against the gate and thereby preventing the drive gear from rotating in the second angular direction to the third angular position;

moving the gate from a blocking position, where the gate prevents the engagement member from angularly bypassing the gate, and an unobstructed position, where the gate is moved to allow the drive gear to rotate to the third angular position; and rotating the drive gear to the third angular position and thereby transitioning the first and second blades to the over-centered position.

19. The method of claim 18, wherein the rotation limiter system further includes a spring compliantly mounted to the gate to naturally bias the gate to the blocking position, and a release pin receivable within an aperture defined in the drive housing and engageable with the gate, the method further comprising:

advancing the release pin into the aperture; and engaging the gate with the release pin and thereby transitioning the gate from the blocking position to the unobstructed position.

20. An end effector for a surgical tool, comprising:

a wrist including a distal clevis, an axle mounted to the distal clevis, and first and second actuation pulleys rotatably mounted to the axle and rotatable about a pivot axis extending through the axle, each actuation pulley providing an actuation boss eccentric to the pivot axis;

a first blade with a first locking portion and a first terminal end defining a first gap between the first blade and the first terminal end, wherein the first blade is pivotably coupled to the actuation boss of the first actuation pulley; and a second blade with a second locking portion and a second terminal end defining a second gap between the second blade and the second terminal end, wherein the second blade is rotatably coupled to the first blade at a center pin and pivotably coupled to the actuation boss of the second actuation pulley, wherein the first and second blades are movable between open and closed positions by rotating the first and second actuation pulleys such that the actuation boss of each actuation pulley remains proximal to a centerline of the axle, wherein the first and second blades are movable to an over-centered position by rotating the first and second actuation pulleys such that the actuation boss of each actuation pulley is located distal to the centerline, and wherein moving the first and second blades to the over-centered position exposes the actuation boss of each actuation pulley, thereby allowing the first and second blades to be removed.

* * * * *